US00PP34204P2

(12) United States Plant Patent
Hall

(10) Patent No.: US PP34,204 P2
(45) Date of Patent: May 3, 2022

(54) ***LAVANDULA* PLANT NAMED '150GY007'**

(50) Latin Name: *Lavandula angustifolia*
Varietal Denomination: 150GY007

(71) Applicant: Elsie K. Hall, Linkwater (NZ)

(72) Inventor: Elsie K. Hall, Linkwater (NZ)

( * ) Notice: Subject to any disclaimer, the term of this patent is extended or adjusted under 35 U.S.C. 154(b) by 0 days.

(21) Appl. No.: 17/300,658

(22) Filed: Sep. 14, 2021

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445, 226
CPC ... A01H 5/02; A01H 5/12; A01H 5/00; A01H 6/50; A01H 6/502
See application file for complete search history.

(56) References Cited

U.S. PATENT DOCUMENTS

PP23,899 P2 * 9/2013 Beekenkamp ..... A01H 5/02 Plt./445

OTHER PUBLICATIONS

Masar. Vimeo Lavandula Kiwiflora Thumbelina 2020, retrieved on Oct. 19, 2021, retrieved from the Internet at https://vimeo.com/451728396, 2 pp. (Year: 2020).*

* cited by examiner

*Primary Examiner* — June Hwu

(57) ABSTRACT

A new cultivar of *Lavandula* plant named '150GY007' that is characterized by a dwarf compact habit, large numbers of purple-blue flowers on short stems, a long flowering period and blooming in the first year without vernalization.

1 Drawing Sheet

Botanical classification: *Lavandula angustifolia.*
Variety denomination: '150GY007'.

BACKGROUND OF THE INVENTION

The present invention relates to a new and distinct cultivar of *Lavandula* plant botanically known as *Lavandula angustifolia* and hereinafter referred to by the cultivar name '150GY007'.

'150GY007' originated from a bed of open pollinated female or seed parent plants of *Lavandula angustifolia* 'Thumbelina Leigh' (U.S. Plant Pat. No. 15,231) in the spring of 2015 in Blenheim, New Zealand. The exact male or pollen parent is unknown. The resulting seeds were collected in December of 2015 and subjected to 150 grays of radiation in January of 2016. These seeds were subsequently planted and grown. The cultivar '150GY007' was selected by the inventor in December of 2017 in a controlled environment as a single plant within the progeny of the stated cross in a cultivated area of Auckland, New Zealand.

Asexual reproduction of the new cultivar '150GY007' first occurred by tissue culture and terminal cuttings in October of 2018 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Lavandula* cultivar '150GY007'. These traits in combination distinguish '150GY007' as a new and distinct cultivar apart from other existing varieties of *Lavandula* known by the inventor.

1. *Lavandula* '150GY007' exhibits a dwarf compact habit.
2. *Lavandula* '150GY007' exhibits large numbers of purple-blue flowers on short stems.
3. *Lavandula* '150GY007' exhibits a long flowering period.
4. *Lavandula* '150GY007' blooms in the first year without vernalization.

The closest comparison cultivars are *Lavandula* 'Hidcote' (not patented) and the female parent plant *Lavandula* 'Thumbelina Leigh'. '150GY007' is distinguishable from 'Hidcote' by the following characteristics:

1. *Lavandula* '150GY007' exhibits a dwarf compact habit. In comparison, the plant size of 'Hidcote' is larger in overall height and width.
2. *Lavandula* '150GY007' exhibits short flower spikes on short peduncles. In comparison, 'Hidcote' has longer flower spikes and longer peduncles.
3. *Lavandula* '150GY007' exhibits a long flowering period, spring through autumn. In comparison, 'Hidcote' only blooms during summer.
4. *Lavandula* '150GY007' blooms in the first year without vernalization. In comparison, 'Hidcote' requires vernalization.
5. *Lavandula* '150GY007' exhibits green leaves. In comparison, the leaves of 'Hidcote' are silver-grey.

'150GY007' is distinguishable from the female parent plant *Lavandula* 'Thumbelina Leigh' by the following characteristics:

1. *Lavandula* '150GY007' exhibits a dwarf compact habit. In comparison, the plant size of the female parent plant is larger in overall height and width.

2. *Lavandula* '150GY007' exhibits short peduncles. In comparison, the female parent plant has longer peduncles.
3. *Lavandula* '150GY007' exhibits a long flowering period, spring through autumn. In comparison, the female parent plant only blooms during summer.
4. *Lavandula* '150GY007' blooms in the first year without vernalization. In comparison, the female parent plant requires vernalization.
5. *Lavandula* '150GY007' exhibits dark violet-blue flower buds. In comparison, the flower buds of the female parent plant are lighter violet-blue in color.

BRIEF DESCRIPTION OF THE DRAWING

The accompanying photograph illustrates the distinguishing traits of *Lavandula* '150GY007'. The photograph shows an overall view of a 15 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Lavandula* cultivar named '150GY007'. Data was collected in Oxnard, Calif. from 18 week old plants grown outdoors in 9 cm. diameter containers. The time of year was Spring and the temperature range was 15-25 degrees Centigrade during the day and 8-15 degrees Centigrade at night. The light level was natural light level. No photoperiodic treatments or growth retardants were used. Color determinations are in accordance with The Royal Horticultural Society Colour Chart 2007 edition, except where general color terms of ordinary dictionary significance are used. The growing requirements are similar to the species. '150GY007' has not been tested under all possible conditions and phenotypic differences may be observed with variations in environmental, climatic, and cultural conditions, however, without any variance in genotype.

Botanical classification: *Lavandula angustifolia* '150GY007'.
Annual or perennial: Perennial.
Parentage: '150GY007' originated from the induced mutation of open pollinated seeds collected from the female or seed parent, *Lavandula angustifolia* 'Thumbelina Leigh'.
Plant type: Herbaceous perennial.
Growth habit: Compact dwarf flattened dome.
Plant shape: Inverted cone.
Suitable container size: 9 to 15 cm. pots.
Plant height to top of foliage: Average 8.0 cm.
Plant height to top of floral plane: Average 15.0 cm.
Plant width: Average 15.0 cm.
Vigor: Moderate.
Growth rate: Moderate.
Low temperature tolerance: USDA zone 5.
High temperature tolerance: 30° Centigrade.
Propagation: Tissue culture and terminal cuttings.
Time to produce a rooted cutting (summer): 28 days at 23° C.
Crop time: Approximately 18 weeks in Oxnard, Calif.
Root system: Fine and fibrous.
Stem:
- *Branching habit*.—Profuse basal branching, all branches arise from base.
- *Pinching*.—Single pinch after establishment of rooted cutting.
- *Number of branches*.—Average 25.
- *Branch dimensions*.—Average 1.25 mm. in width and 11 cm. in length.
- *Branch strength*.—Strong.
- *Branch angle*.—Average 0 degrees from vertical.
- *Pubescence*.—Puberulent.
- *Internode length*.—Average 4.0 mm. between nodes.
- *Shape*.—Square in cross-section.
- *Branch color*.—143C.

Foliage:
- *Leaf arrangement*.—Typically opposite, occasionally alternate.
- *Compound or single*.—Single.
- *Quantity of leaves per branch*.—Average 18.
- *Leaf shape*.—Lanceolate.
- *Leaf aspect*.—Upper surface longitudinally convex, lower surface concave.
- *Leaf apex*.—Acute.
- *Leaf base*.—Truncate.
- *Leaf dimensions*.—Average 25.0 mm. in length and 3.0 cm. in width.
- *Leaf texture upper surface*.—Slightly rough.
- *Leaf texture lower surface*.—Slightly rough.
- *Leaf luster upper surface*.—Matte.
- *Leaf luster lower surface*.—Matte.
- *Pubescence*.—Puberulent (both surfaces).
- *Leaf margin*.—Entire, revolute.
- *Venation pattern*.—Parallel, mid-vein depressed on upper surface and raised on lower surface.
- *Leaf color* (*upper surface*).—191A.
- *Leaf color* (*lower surface*).—143C.
- *Vein color* (*upper surface*).—145A.
- *Vein color* (*lower surface*).—145A.
- *Leaf fragrance*.—Strong lavender fragrance.
- *Leaf attachment*.—Sessile.

Flower:
- *Inflorescence type*.—Terminal spike.
- *Inflorescence shape*.—Cylindrical shaped spike.
- *Inflorescence dimensions*.—Average 21.0 mm. in length and 15.0 mm. in diameter.
- *Quantity of inflorescence*.—Average 25 per plant.
- *Quantity of flowers and buds per inflorescence*.—Average 25 per spike.
- *Average number of whorls per spike*.—5.
- *Length from second whorl to top of spike*.—Short.
- *Distance between whorls*.—Very short.
- *Natural flowering season*.—Spring to Autumn.
- *Time to flower or response time*.—3 months from rooting.
- *Flower type and form*.—Corolla tube with 5 lobes.
- *Bud length*.—Average 3.0 mm.
- *Bud diameter*.—Average 2.0 mm.
- *Bud shape*.—Ovoid.
- *Bud texture*.—Glabrous.
- *Bud luster*.—Slightly glossy.
- *Bud color*.—N92C.
- *Rate of flower opening*.—14 days from first bud to last flower opening.
- *Flower aspect*.—Upward and outward.
- *Flower shape*.—Petals fused into corolla tube which subtends 5 free petaloid lobes.
- *Corolla tube dimensions*.—Average 2.5 mm. in diameter and 7.0 mm. in depth.

*Corolla tube color*.—NN155D (both surfaces).

*Corolla tube texture*.—Glabrous, translucent towards base.

*Petaloid lobes* (2 *upper lobes*).—Each lobe average 4.0 mm. in length and 3.0 mm. in width, color 85A to 85B on both surfaces, margins N87C, apex rounded, texture smooth on both surfaces.

*Petaloid lobes* (3 *lower lobes*).—Each lobe average 3.0 mm. in length and 3.0 mm. in width, color 85A to 85B on both surfaces, margins N87C, apex rounded, texture smooth on both surfaces.

*Flower longevity*.—5 to 7 days.

*Flower longevity as a cut flower*.—5 to 7 days.

*Persistent or self-cleaning*.—Self-cleaning.

Bracts:

*Infertile bracts*.—Absent.

*Fertile bracts*.—Absent.

Bracteoles: At base of spike are 1 to 2 bracteoles, 2.5 mm. in length.

Calyx: Tubular in shape, dimensions average 4.5 mm. in length and 2.5 mm. in width, sepals fused to form calyx tube.

Sepals:

*Sepal arrangement*.—Fused, parallel, slightly ribbed.

*Number of sepals*.—5.

*Sepal dimensions*.—Average 4.5 mm. in length and 1.5 mm. in width.

*Sepal shape*.—Lanceolate.

*Sepal tip*.—Acute.

*Sepal base*.—Truncate.

*Sepal color* (*both sides*).—N92C.

Peduncle:

*Peduncle dimensions*.—Average 4.0 cm. in length and 1.2 mm. in diameter.

*Lateral branching on peduncle above foliage*.—Absent.

*Aspect of flowering stems at full flowering*.—Central stems erect, outer stems leaning outward up to 20 degrees from vertical.

*Peduncle strength*.—Strong.

*Peduncle texture*.—Glabrous, smooth.

*Peduncle color*.—143C.

Reproductive organs:

*Stamen number*.—4 (2 posterior, 2 anterior).

*Anther shape*.—Reniform.

*Anther length*.—Average 0.4 mm.

*Anther width*.—Average 0.4 mm.

*Anther color*.—N200A.

*Filament length*.—Average 1.5 mm.

*Filament color*.—NN155D.

*Amount of pollen*.—None.

*Number of pistils*.—1.

*Pistil length*.—Average 2.5 mm.

*Pistil diameter*.—Average 0.2 mm.

*Stigma shape*.—Ellipsoid.

*Stigma color*.—NN155D.

*Style length*.—Average 4.0 mm. in length.

*Style color*.—NN155C.

*Ovary shape*.—Globe shaped, 0.5 mm. in diameter.

*Ovary color*.—146C.

Fruit and seed: '150GY007' has not produced fruit or seed to date.

Disease and pest resistance: Disease and pest resistance has not been observed.

The invention claimed is:

1. A new and distinct variety of *Lavandula* plant named '150GY007' as described and illustrated.

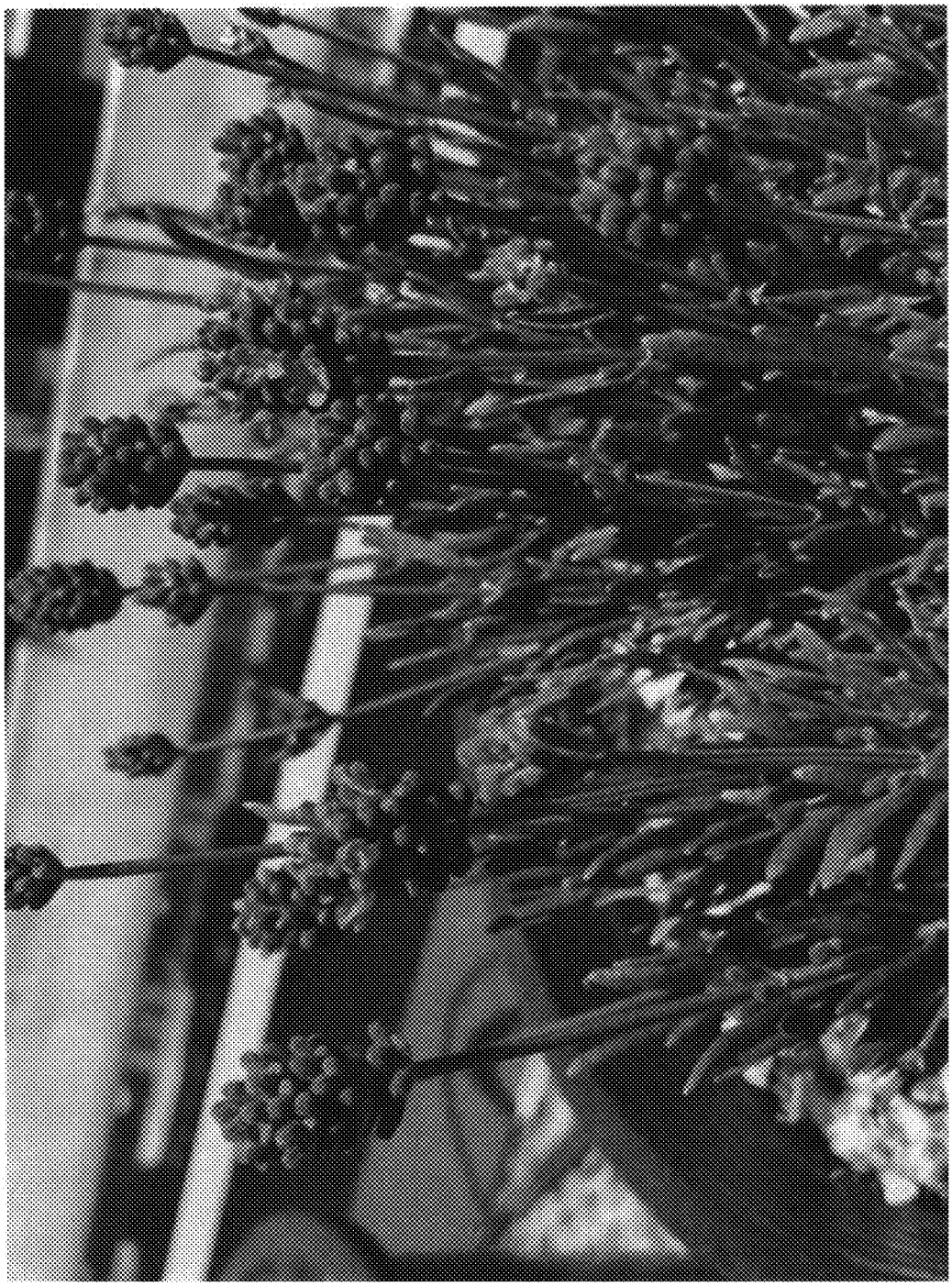

* * * * *